(12) United States Patent
Smith

(10) Patent No.: US 8,784,347 B1
(45) Date of Patent: Jul. 22, 2014

(54) HIGH-BACK GLUTEAL SHAPING COMPRESSION GARMENT

(71) Applicant: Veronica C. Smith, South Richmond, CA (US)

(72) Inventor: Veronica C. Smith, South Richmond, CA (US)

(*) Notice: Subject to any disclaimer, the term of this patent is extended or adjusted under 35 U.S.C. 154(b) by 0 days.

(21) Appl. No.: 13/971,370

(22) Filed: Aug. 20, 2013

Related U.S. Application Data

(60) Provisional application No. 61/757,067, filed on Jan. 25, 2013.

(51) Int. Cl.
*A61F 5/00* (2006.01)
*A61F 13/00* (2006.01)
*A61F 5/40* (2006.01)

(52) U.S. Cl.
CPC .................................... *A61F 5/40* (2013.01)
USPC ................... 602/19; 602/60; 602/61; 602/62; 450/99

(58) Field of Classification Search
USPC ................ 602/19, 60–64; 128/873–875, 882; 2/404–407, 409, 69; 450/20, 82, 95, 450/98, 99, 115–118, 18
See application file for complete search history.

(56) References Cited

U.S. PATENT DOCUMENTS

| | | | | |
|---|---|---|---|---|
| 2,332,141 A * | 10/1943 | Greene | ........................... | 450/98 |
| 2,569,229 A * | 9/1951 | Cooper | ........................... | 450/99 |
| 2,668,953 A * | 2/1954 | Tofanelli | ........................ | 450/99 |
| 3,375,829 A * | 4/1968 | Brennan et al. | ............... | 450/115 |
| 5,611,722 A * | 3/1997 | Osborne | ........................ | 450/99 |
| 5,708,986 A * | 1/1998 | Belardinelli | .................... | 450/99 |
| 5,954,564 A * | 9/1999 | Ganz | ............................... | 450/99 |
| 6,182,297 B1 * | 2/2001 | Duren et al. | ....................... | 2/228 |
| 7,143,453 B2 * | 12/2006 | Duran | .............................. | 2/409 |
| 8,105,256 B1 * | 1/2012 | Ariza | .............................. | 602/19 |
| 8,430,830 B1 * | 4/2013 | Ariza | .............................. | 602/19 |

* cited by examiner

*Primary Examiner* — Kim M Lewis
(74) *Attorney, Agent, or Firm* — David E. Newhouse, Esq.

(57) ABSTRACT

A post-surgery, high-back, compression garment is described for post-operatively immobilizing surgically corrected tissues to ensure proper healing and provide molded gluteal-shaping power-net domes that preserve desired anatomic curvature enhancements and corrections in the gluteal regions of the human body during convalescence following contouring gluteoplasty procedures.

9 Claims, 13 Drawing Sheets

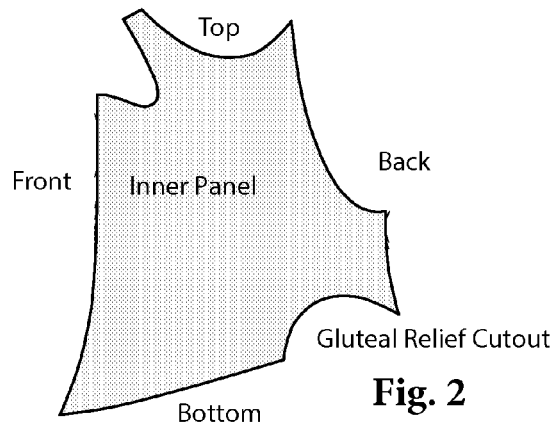
Fig. 2
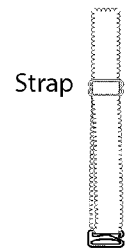
Fig. 5
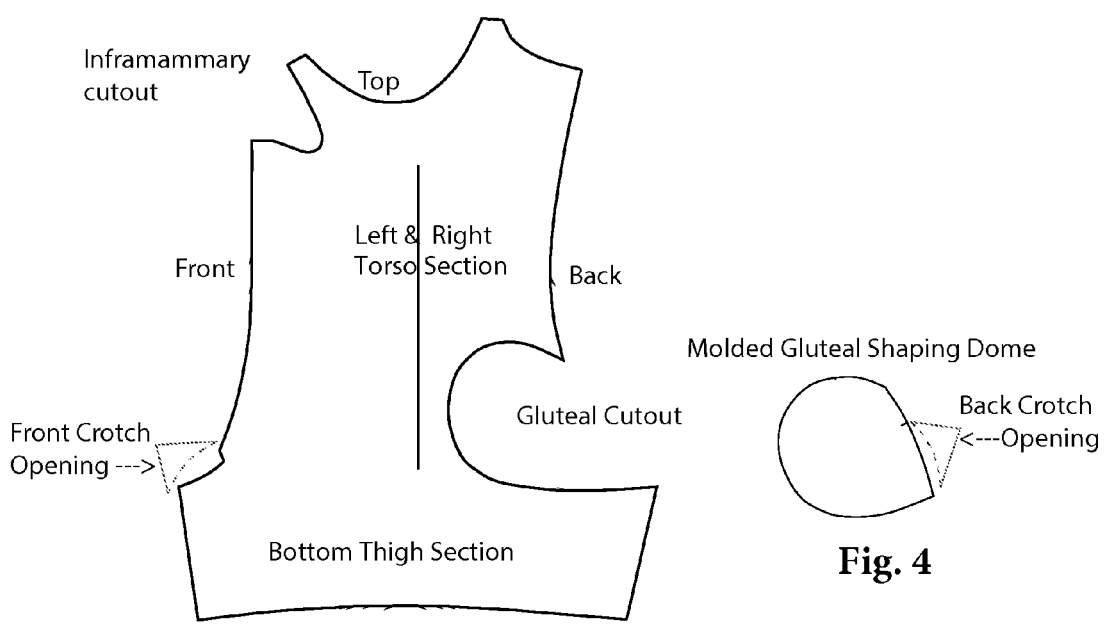
Fig. 3
Fig. 4

HIGH-BACK GLUTEAL SHAPING COMPRESSION GARMENT

RELATED APPLICATIONS

This application claims all benefits applicable under 35 U.S.C. §119(e) related to U.S. Provisional Patent Application Ser. No. 61/757,067 filed by the Applicant on 25 Jan. 2013 entitled "HIGH-BACK GLUTEAL SHAPING GIRDLE", and incorporates U.S. Provisional Patent Application Ser. No. 61/757,067, in its entirety, by reference into this application.

BACKGROUND OF THE INVENTION

1. Field of the Invention

This invention relates generally to post surgery medical compression garments, and in particular to a high-back compression garment that post-operatively immobilizes surgically corrected tissues to ensure proper healing and provides molded gluteal-shaping power-net domes that preserve desired anatomic curvature enhancements and corrections in the gluteal regions of the human body during convalescence following contouring gluteoplasty procedures.

2. Description of the Prior Art

Medical compression garments assist healing processes and improve post operative results of reconstructive or aesthetic (plastic) surgery procedures such as augmentation, liposculpture (fat-transfer liposuction and lipofilling), that disturb the cohesion between the dermis, subcutaneous fat, and muscle layers. In particular, such procedures bruise connective tissues, traumatize capillaries and blood vessels, and compromise the lymphatic fluid distribution system. Serum and blood seep into adjacent tissues, causing swelling (hematomas, seromas) lymphedema and inflammation, all of which, if not constrained will stretch epidermis and dermis skin layers affecting adherence of the affected dermal layers to the underlying tissues.

In the case of liposculpture procedures, adipose (fatty) tissue is harvested from donor regions of a patient's body by aspirating the tissue using a cannula typically coupled with a power assisted suction device. The harvested tissue is flowable, i.e. a liquid. Suitable donor regions may include mammary, abdominal, pubic, flank, thigh, gluteal, or trochanter (hip) regions of the human body. Sites for adipose tissue harvest are also frequently determined by aesthetic concerns and desires of the patient and by medical safety profiles observed by the plastic surgeon. While the harvested tissue can be re-infused directly to a different region of the body, it is more typically purified to remove debris and/or contaminants including blood, serum, proteases, lipases, lipids, other oils, tumescent harvest fluids, and/or other impurities collected in the liposuction procedure. The purified tissue may then be stored and/or further processed for enrichment of healthy adipocytes and regenerative cells such as pluripotent cells. It can also be supplemented with growth factor compounds associated with regenerative cells obtained from other sources for increasing survival rate of the tissue by promoting new blood vessel formation (angiogenesis and arteriogenesis) within the tissue upon re-infusion (See for example U.S. Pat. No. 8,246,947, Hederick, Mark H. et al; & U.S. Patent Pre-Grant Publication App. No. 20120219627, Van Epps; Dennis E.; et al.).

Re-infusion-re-implantation of liquid adipose tissue alone, or in processed combination for augmenting and lipofilling is preferably accomplished at controlled, metered rates using a cannula mated with a syringe and plunger. (See U.S. Pat. No. 8,133,208, H. E. Hetherington.) The re-infused/implanted adipose tissue, whether freshly harvested or processed, flows and collects within selected lipofill regions inflating the affected anatomical configuration of the region responsive to pressure gradients induced or created by the tissues surrounding of the lipofill. There will be some loss of tissue hence volume in the lipofill region during healing attributable to necrosis of both the re-infused/implanted adipose tissue combinations and surrounding tissues until adequate revascularization processes, (angiogenesis and arteriogenesis) and related inter-cell structural fusion processes integrate the re-infused/implanted adipose tissue combinations with the surrounding tissues. Until integration, the re-infused/implanted adipose tissue will continue to move about in the lipofill volume and even diffuse into the surrounding tissues responsive to pressure gradients due to muscular contraction and relaxation, gravity, and more particularly, by compressive stresses provided by properly designed and fitted post surgery compression garments.

Properly designed and fitted medical compression garments provide tension gradients that pressurize the underlying, disturbed, malleable tissue layers both for assuring contact for proper healing and for contouring anatomical surfaces to promote, engender, or support a desired therapeutic, structural, or cosmetic benefit. "High" pressure compression garments can provide pressure gradients, ranging up to 15 to 20 torr across an anatomical body surface of a patient that will induce pressure gradients in the underlying malleable tissues for disbursing and directing fluids (gases and liquids) seepage and diffusion of such fluids into underlying lower pressure regions. Given, accurate compression and patient compliance, wearing a medical compression garment significantly affects outcome. Patients who comply with a treating plastic surgeon's prescribing recommendations to wear a selected properly designed compression garment report and enjoy a greater sense of overall satisfaction associated with the results their procedure, particularly those reporting 100% compliance versus those who wear a compression garment less than a prescribed or recommended time.

Also, patient compliance with his or her treating plastic surgeon is directly linked to a compression garment that provides accurate compression, properly fits the patient's body, is designed for good hygiene, and is attractive and comfortable to wear.

SUMMARY OF THE INVENTION

Post-surgery, high-back medical liposculpting gluteal compression garments are described that include an open-top, torso sleeve formed by joined symmetrical left and right inner and outer elastic power-net fabric panels having elastic seamed, underarm reliefs between front and back shoulder-strap anchor tabs, an elastic seamed, scalloped back collar and a front elastic inframammary chest seam, left and right thigh sleeves including a convenient crotch opening for compressing the torso, tummy and thighs of a human body, while incorporating joined, symmetrical, left and right molded, gluteal-shaping, elastic power-net fabric domes for shaping the gluteal region (buttocks) of a human body.

BRIEF DESCRIPTION OF THE FIGURES

FIG. 2 presents the cut-out pattern for symmetrical (left and right) inner elastic power-net fabric torso panels the of the high-back gluteal shaping compression garment.

FIG. 3 presents the cut-out pattern for the symmetrical (left and right) outer elastic power-net fabric panels of the high-back gluteal shaping compression garment.

FIG. 4 presents the cut-out pattern for the symmetrical (left and right) molded power-net fabric gluteal panels of the high-back gluteal shaping compression garment FIG. 5 presents an image of an adjustable shoulder strap for the high-back gluteal shaping compression garment.

DESCRIPTION OF PREFERRED AND EXEMPLARY EMBODIMENTS

Figure 7A:
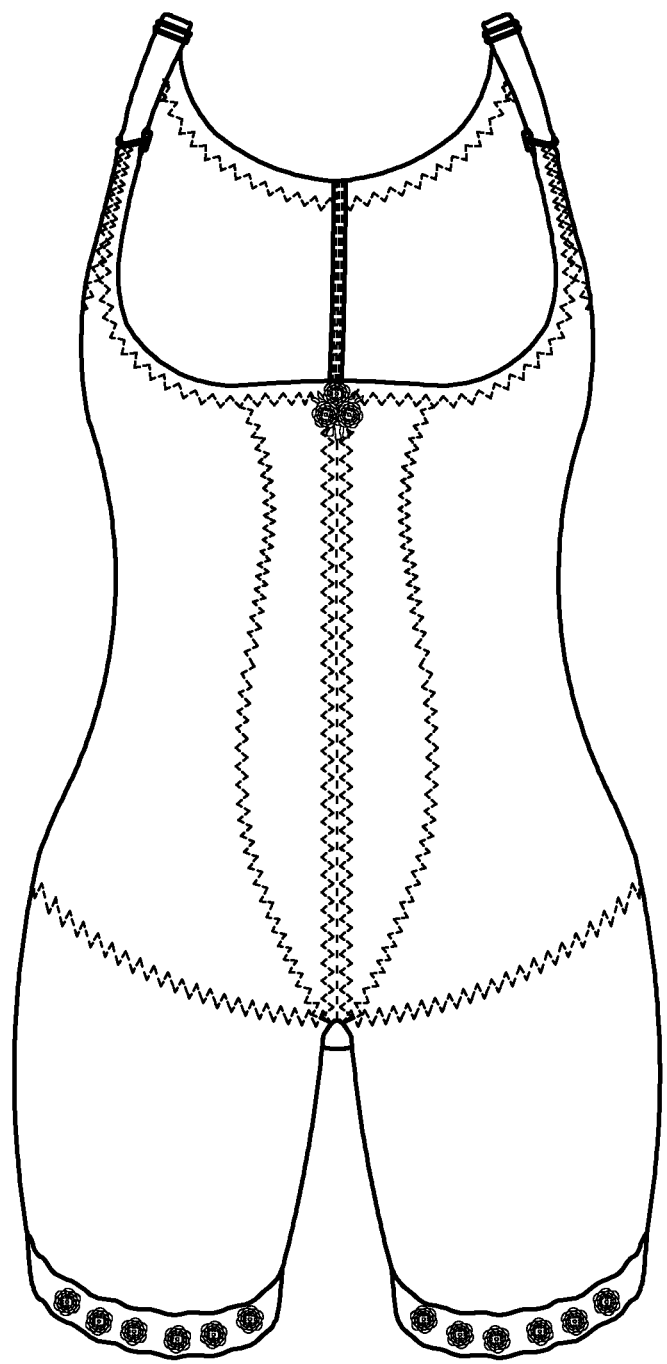
FIGS. 7a-7b respectively present a front exterior view and a front interior view of a non-zippered embodiment of a high-back gluteal shaping compression garment incorporating a shaped, abdominal, power-net fabric, tummy panel with symmetrical left and right side edges secured within the compression garment
Figure 7B:
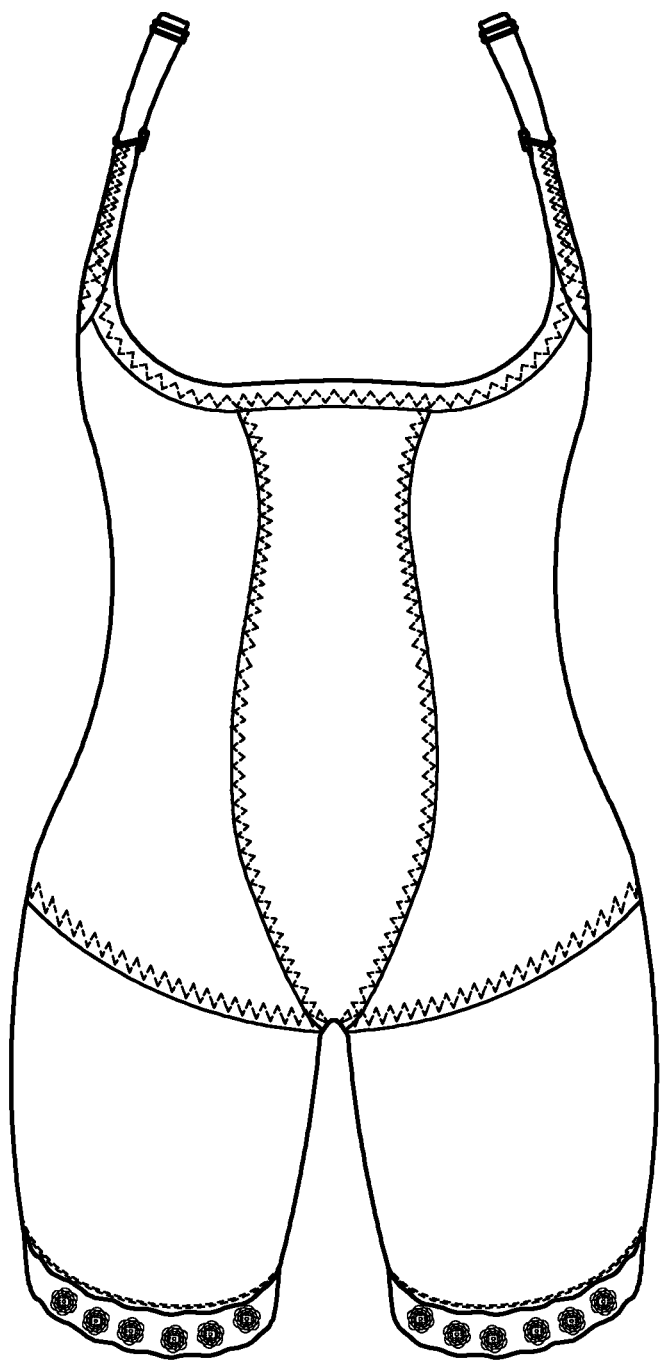
Figure 10A:
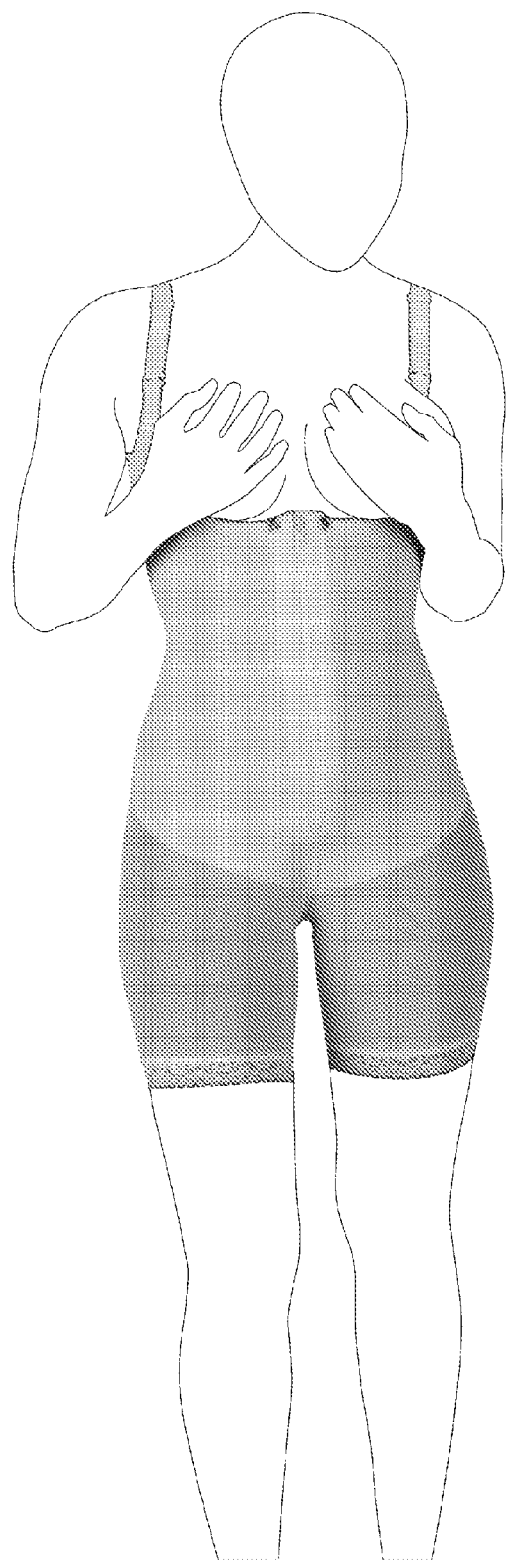
FIGS. 10a-10b present tinted modeled images respective depicting front perspective views of the zippered and non-zippered embodiments of the claimed high-back gluteal shaping compression garment.
Figure 10B:
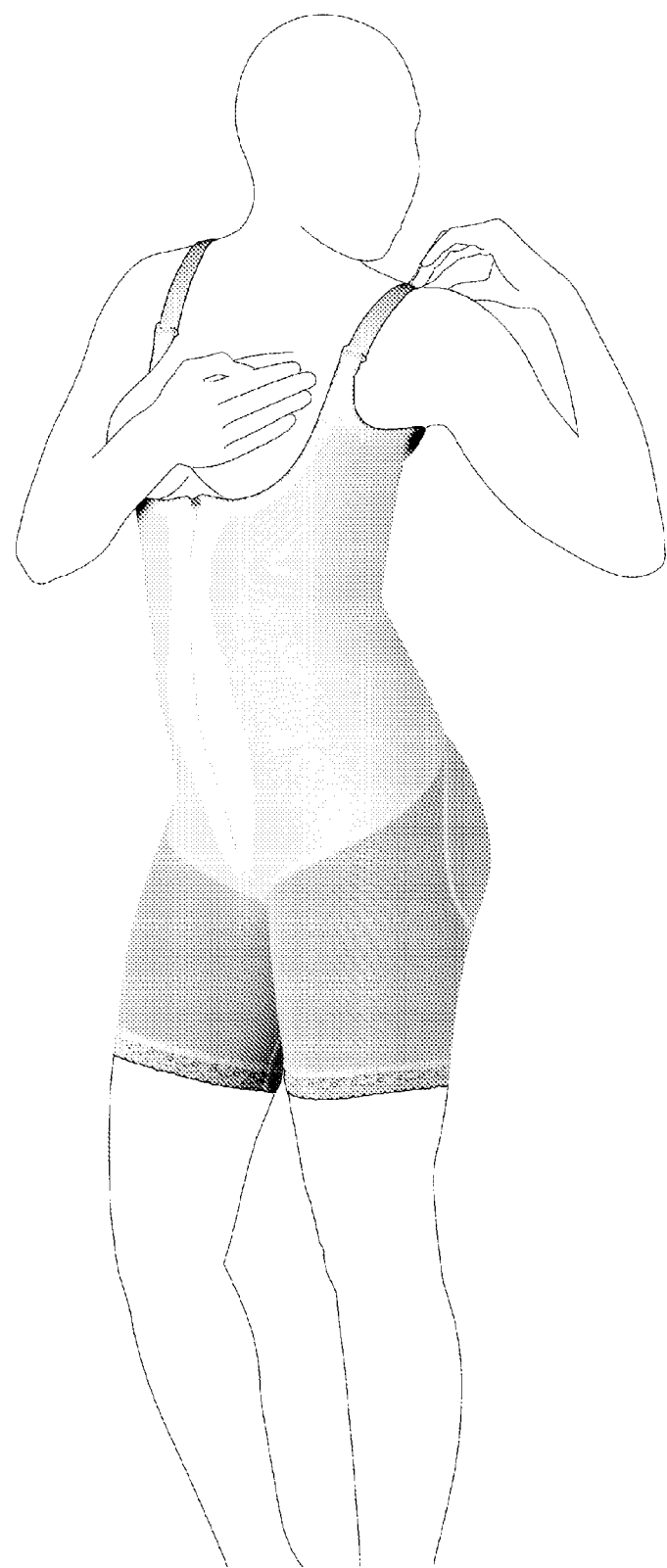

With reference to the figures, two embodiments of the post surgery, medical liposculpting high-back compression garments are illustrated, a front zippered embodiment (See FIGS. 1a-1d, FIGS. 9a-9c & FIG. 10a), and a non-zippered embodiment (See FIGS. 7a & 7b & FIG. 10b). The non-zippered embodiment has an interior symmetrical shaped, centered abdominal, power-net fabric, tummy panel. The distinguishing feature of both embodiments are the joined symmetrical left and right molded, gluteal power-net fabric domes incorporated into the garment secured by elastic seams (FIG. 8).

Figure 10C:
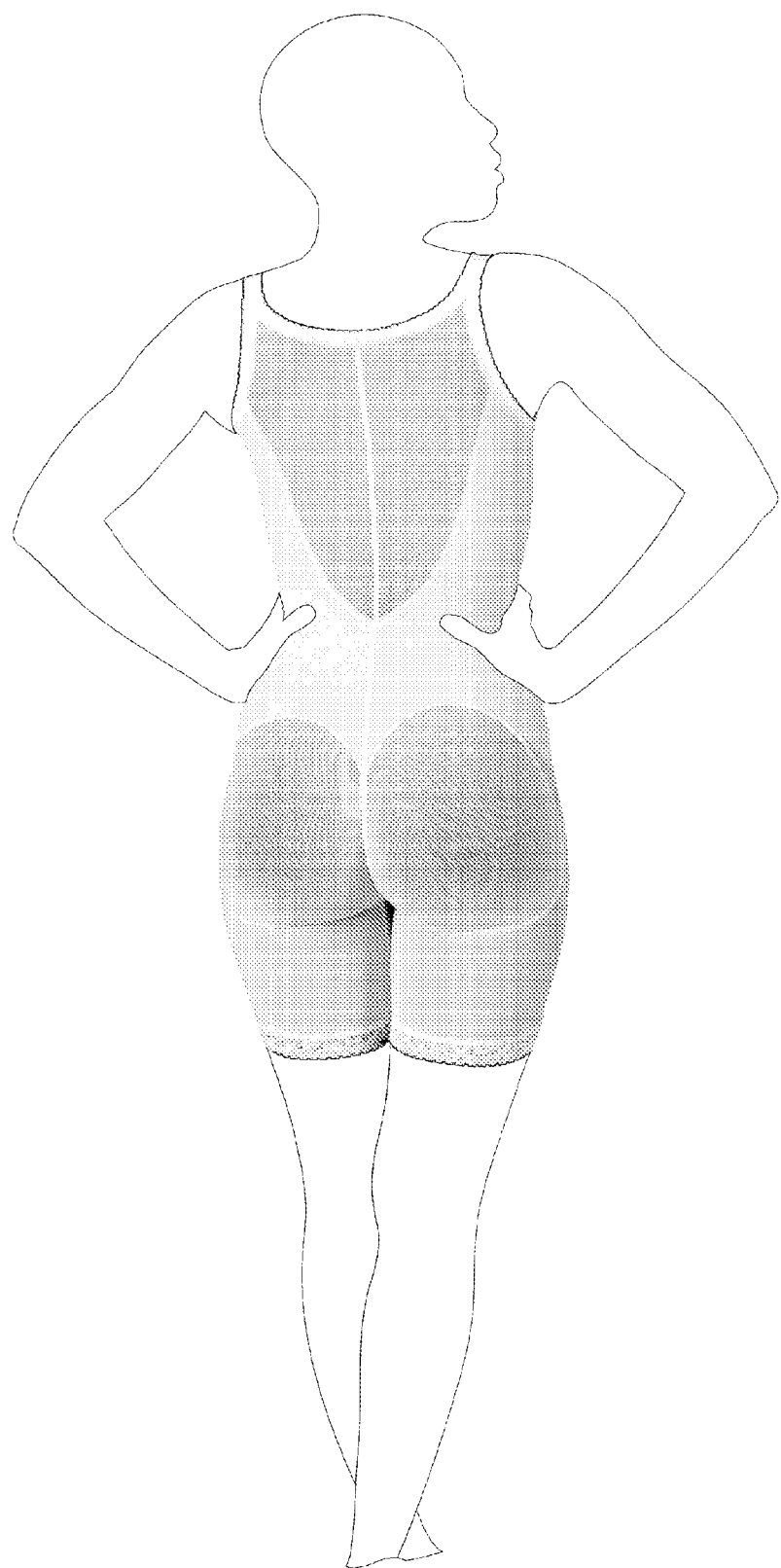
FIG. 10c presents a tinted modeled image depicting a rear perspective view of the high-back gluteal shaping girdle compression garment.

Techniques and machines for molding synthetic fabrics including spandex-nylon blend "power-net" fabrics are well known (See for example U.S. Pat. No. 7,776,770, Wang et al, & U.S. Pat. No. 8,262,434, Falla et al). In more detail, the garment pattern pieces are cut (FIGS. 2-6) and sewn together (FIG. 7). The gluteal panels (FIG. 4) may be molded using a dome molding machine to form a dome (See FIGS. 8-10 of U.S. Pat. No. 7,776,770, Wang et al,) before being sewn into the garment. Alternatively the gluteal panels can the sewn into the garment before molding in which case the seams closing the thigh panels and front torso panels must left open to allow the gluteal panels to be positioned on the machine to form a desired dome.

Figure 8:
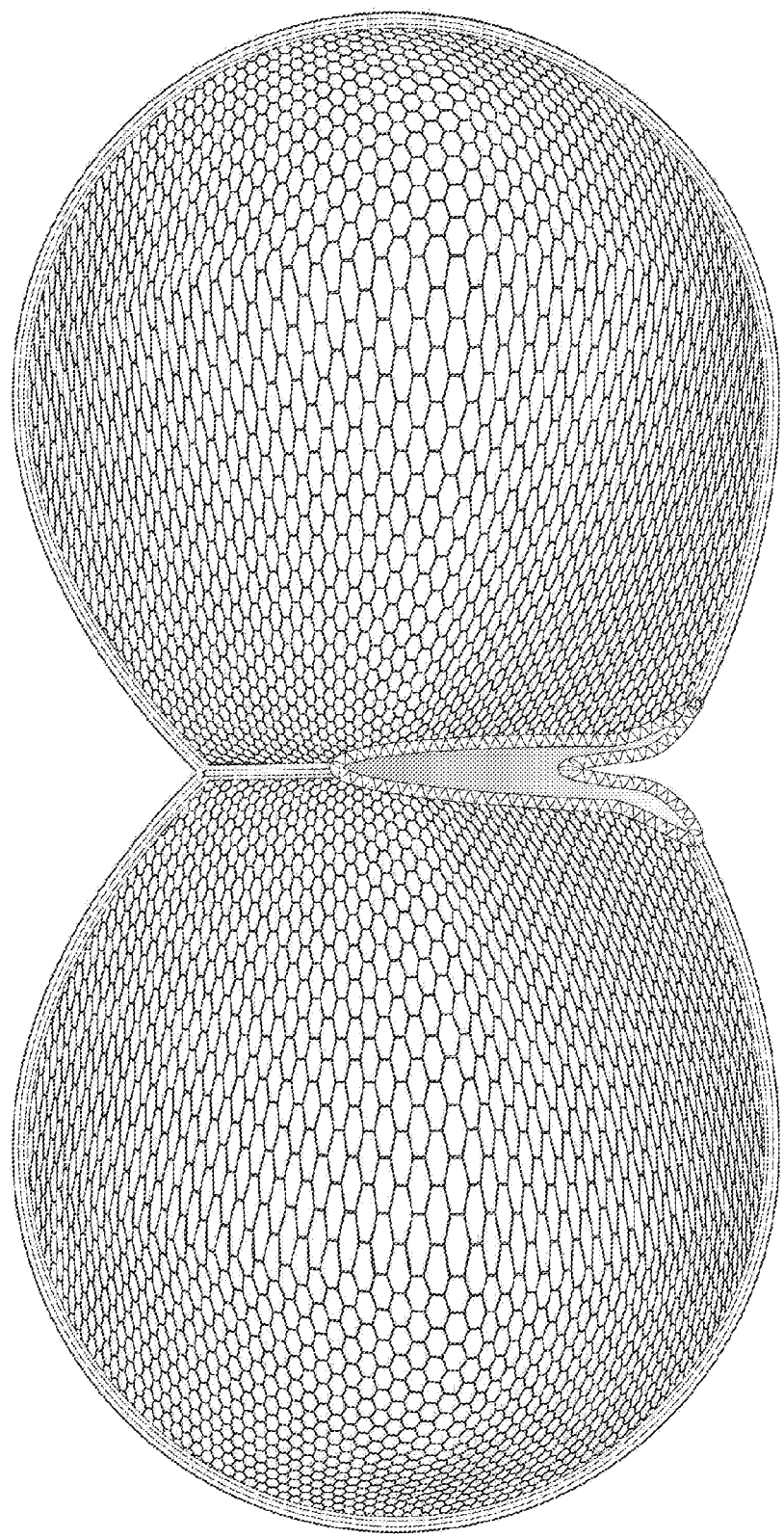
FIG. 8 is a perspective rendering of the joined symmetrical left and right, molded, power-net fabric, gluteal domes of the high-back gluteal shaping girdle compression garment illustrating the change in size of the hexagonal elastane elastic cells of the power-net fabric panels following molding and the crotch opening of the compression garment.
Figure 9A:
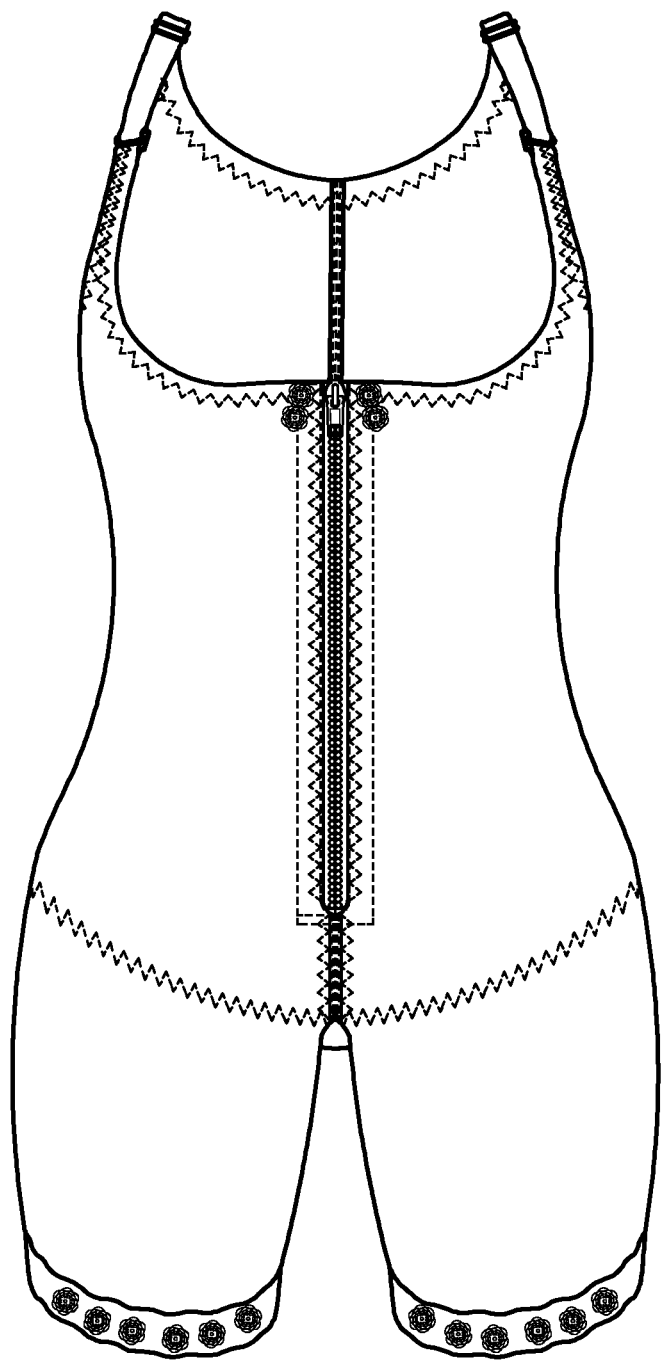
FIGS. 9a-9b present exterior front views of an embodiment of the high-back gluteal shaping compression garment closed by a non-separating zipper with and underlying guard tape.
Figure 9B:
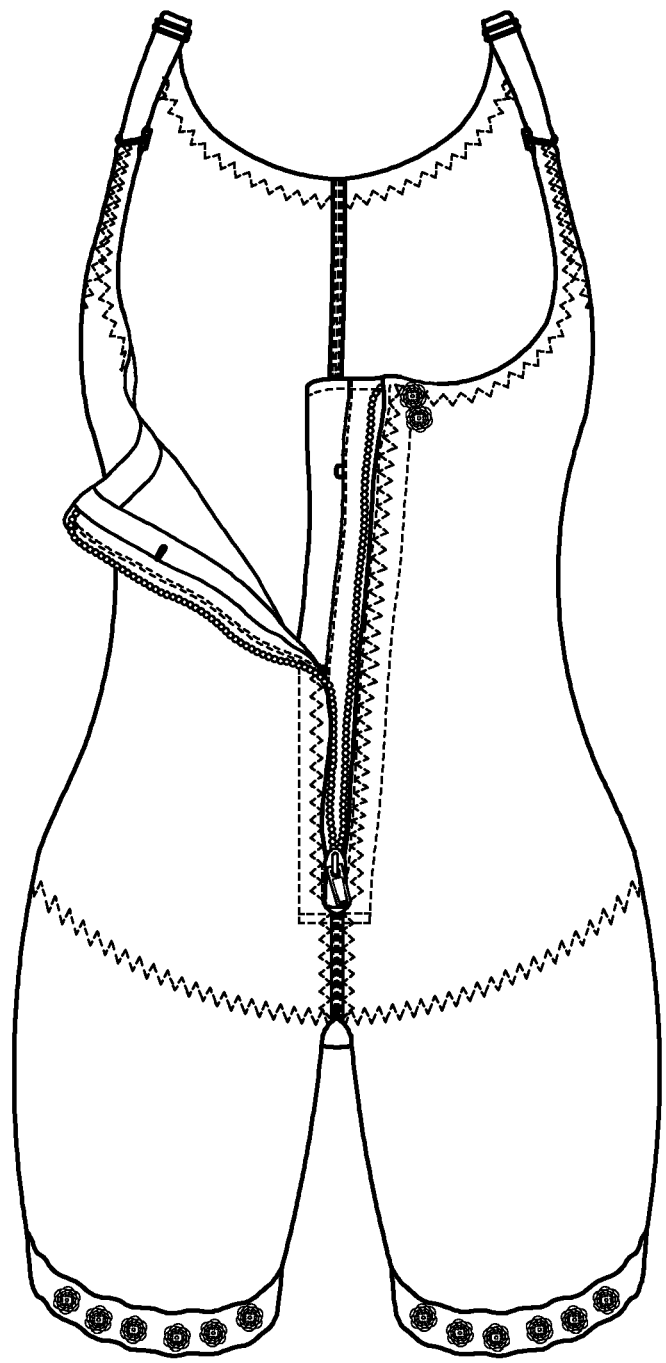
Figure 9C:
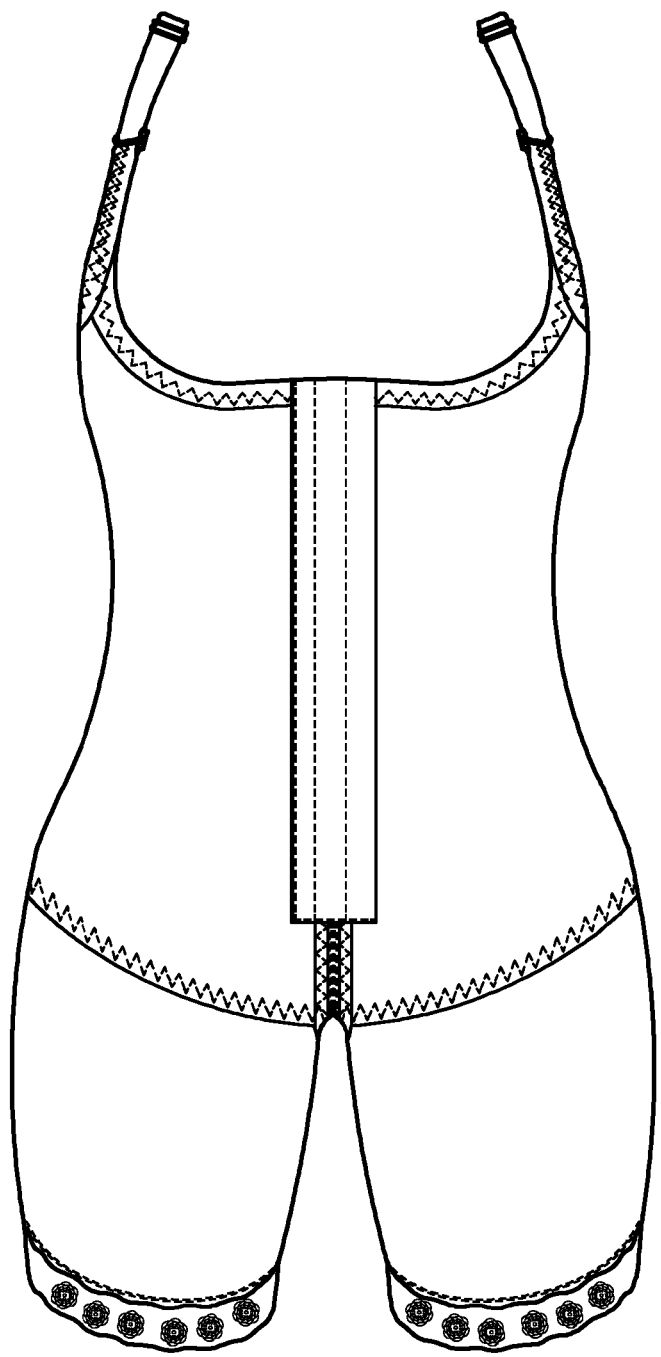
FIG. 9c presents an interior front view of the high-back gluteal shaping compression garment closed by a non-separating zipper.

As illustrated in FIG. 8, the hexagonal cells of the molded power-net fabric dome uniformly expand in circumference toward the top the dome during the forming process. After 'heat setting" the expanded power-net cells retain significant elasticity properties. However, as the area encompassed by a power-net cell increases, the magnitude of compressive stress transferred to underlying malleable tissues will decrease. In effect, the formed gluteal domes establish a pressure gradient in the underlying gluteal tissues that will decrease toward the top of the dome for contouring, while supporting the anatomical surface of the gluteal mass to promote, a desired therapeutic, structural, or cosmetic benefit.

The remaining compressive components of the illustrated embodiments of the high-back compression garment provide therapeutic healing compression to donor regions of the human body from which fatty tissues have may been harvested or otherwise liposculpted. (See E. Goldfinger, Human Anatomy for Artist, Oxford University Press, 1991, pp. 292-293 illustrating the distribution of surface fat pads on idealized male and female human bodies.)

In more detail, turning to FIGS. 2-6, the post surgery liposculpting, medical high-back girdle compression garment includes symmetrical (left and right) inner and outer elastic power-net fabric panels each having top, and bottom, back and back edges (FIGS. 2 & 3). The left and right torso sections of the outer panels each have a top edge with an underarm cut-out between front and back shoulder-strap anchor tabs (FIG. 6), and with a frontal inframammary cutout for establishing a front inframammary line when the left and right torso sections are joined together (see FIGS. 7a & 9a). The front side edges of the left and right the torso sections of the symmetrical outer panels have edge cut-outs for a crotch opening. The back side edges of the left and right torso sections of the symmetrical outer panels have gluteal cutouts curving outwardly and downwardly respectively to the left and right front edge cut-outs for the open crotch (see FIG. 8). The left and right thigh sections of the symmetrical panels each have front side edges respectively extending from the left and right front edge cut-outs for the crotch opening to the bottom edge of the particular power-net fabric panel, and back side edges respectively extending from the left and right back gluteal cut-out locations to the bottom edges of each particular power-net fabric panel.

Figure 1A:
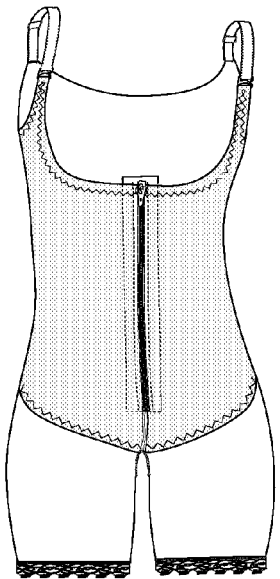
FIGS. 1a & 1b respectively present a frontal, and a back, perspective shell views of a front, zippered embodiment of a high-back gluteal shaping girdle compression garment.
Figure 1B:
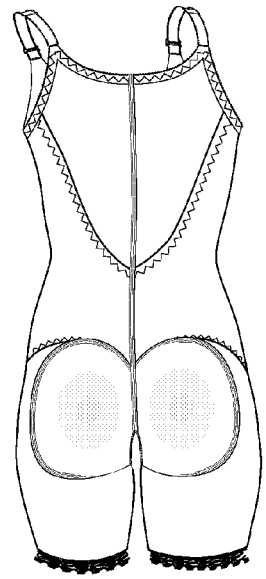
Figure 1C:
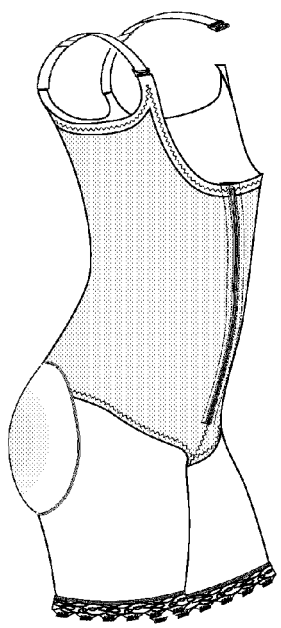
FIGS. 1c & 1d respectively present a right-side-front and a right-side-back of a front zippered embodiment of the high-back gluteal shaping girdle compression garment.
Figure 1D:
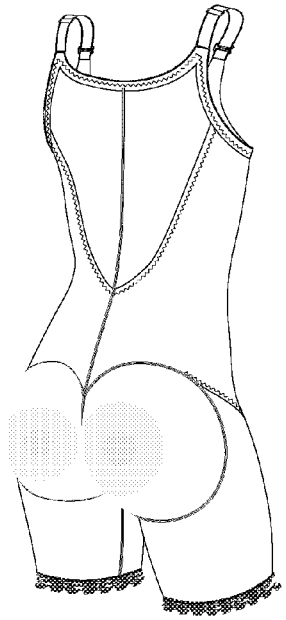
Figure 6:
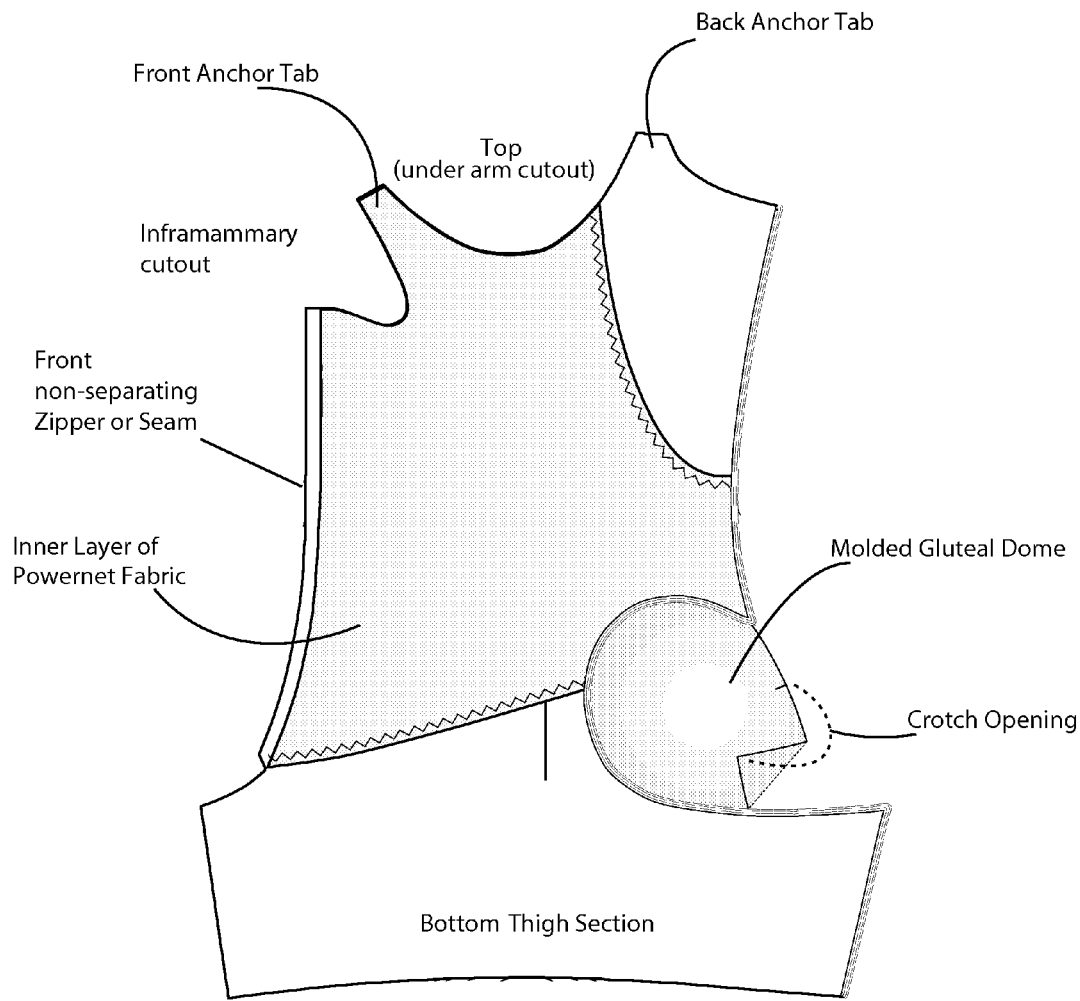
FIG. 6 illustrates how the cut-out of the claimed high-back gluteal shaping compression garment shown in FIGS. 2, 3 & 4 are sewn together.
Figure 7C:
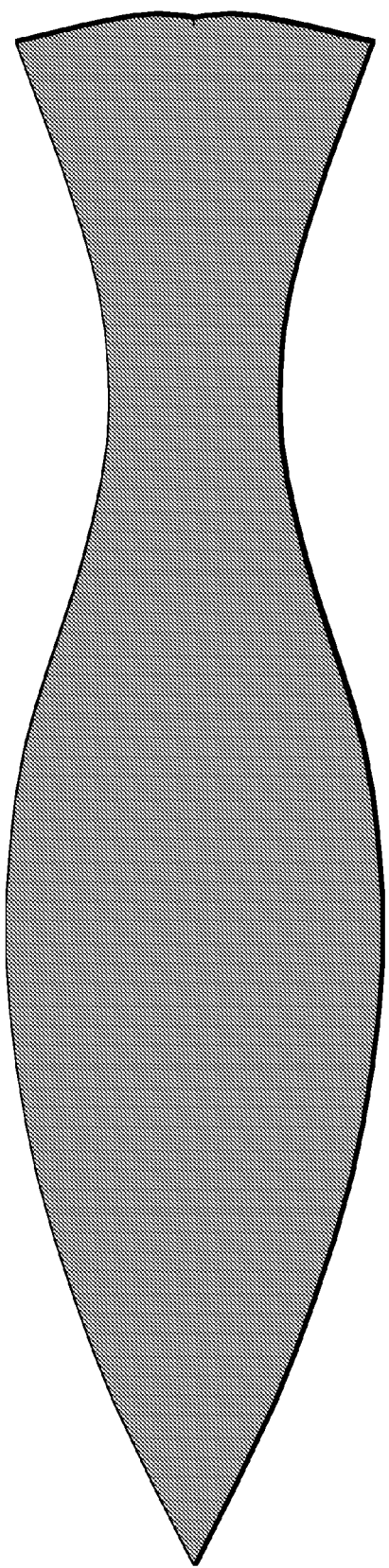
FIG. 7c presents the cutout pattern for the shaped, abdominal, power-net fabric, tummy panel.

Symmetrical (left and right), gluteal-shaping, molded, elastic power-net fabric domes, each having a bottom cut-out for the crotch opening, are respectively secured by elastic seams within left and right back edge gluteal cutouts of the left and right inner and outer elastic power-net fabric panels (FIG. 6).

A central, back elastic seam (see FIGS. 1b, 1d, & 10c) joins the back edges of the left and right torso sections of the outer elastic power-net fabric panels together and the adjacent edges of the left and right molded, gluteal-shaping, elastic power-net fabric domes together below the left and right torso sections extending to the bottom cut-outs of the domes for the crotch opening. Elastic thigh seams (FIG. 1d) respectively join the front and back side edges of the left and the right thigh sections (FIG. 6) forming left and right thigh compression sleeves (FIGS. 1a-1d, 7a, 9a & b, 8 and 10a-c), and provide an elliptically shaped crotch opening in cooperation with the bottom cut-outs of the left and right molded, gluteal-shaping, elastic power-net fabric domes (FIG. 8). As shown in FIG. 8, a folded liner elastic fabric strip is secured by a zigzag stitch seam around elliptical crotch opening reinforcing the respective edges of the crotch cutouts of the thigh sleeves and gluteal-shaping, elastic power-net fabric domes and preserving opening as it stretches underlying a human female crotch. Those artisans skilled in art of compression garment design, should appreciate that the configuration and size of crotch openings can be varied to accommodate different human crotches including male gentiles.

In both the non-zippered and zippered embodiments of the high-back gluteal shaping girdle compression garment, reinforcing elastic fabric strips are elastically secured along, the top back and bottom edges of the power-net fabric panels providing elastic edge underarm reliefs seams between front and back shoulder-strap anchor tabs, a scalloped, elastic edge back collar seam, elastic edge front inframammary torso seam(s) and elastic edge bottom thigh sleeve seams.

Returning to FIGS. 2 & 6, both the embodiments of the high-back gluteal shaping compression garment include symmetrical (left and right) inner power-net fabric torso panels each with top, and bottom, front and back edges. The left and right top edges of the inner power-net fabric torso panels respectively conform to that of, and are incorporated with and secured by the reinforced elastic edge seam with the corresponding top edges the outer power-net fabric panels from the back shoulder-strap anchor tabs across the provided front inframammary top of the garment. The left and right front edges of the inner power-net fabric torso panels respectively conform to and are secured by common seams also securing the front edges of the corresponding left and right front edges of the corresponding torso sections of the outer power-net fabric panels. Elastic seams secure the left and right bottom edges of the of the inner power-net fabric torso panels to the corresponding outer elastic power-net fabric torso panels from the front, top of the crotch opening up and around, along left and right human, inguinal—iliac lines to the back gluteal relief cutouts of the respective panels. The back gluteal relief cutouts of the inner panels are incorporated with and secured by the elastic seams securing the corresponding outer elastic power-net fabric panels to the left and right molded, gluteal-shaping, elastic power-net fabric domes. The left and right back edges of the inner power-net fabric torso panels are respectively secured by elastic seams to the corresponding outer elastic power-net fabric torso panels plunging symmetrically below the scalloped back collar of the joined outer fabric torso panels from the back sections of under-arm cutouts to the central back elastic seam in the small back region of the torso section of the garment above the gluteal relief cutouts. The central back elastic seam secures the lower back edges of the inner fabric torso panels with back edges the torso sections of the outer elastic power-net fabric panels above the gluteal cutouts of the respective panels.

In the zippered embodiment of the high-back gluteal shaping girdle compression garment (see FIGS. 1a-d, 9a-9c, & 10a), an opening torso sleeve is established by a non-separating torso zipper joining the front edges of the torso sections of the respective inner and outer panels together zipping up from a base in a pubic region above the front cut-outs for the crotch opening joining the frontal inframammary cutouts establishing the front inframammary top of the garment. A central front elastic seam joins the back side edges of the left and right torso sections of the inner and outer elastic power-net fabric panels together between the fastener base and the open crotch.

The torso zipper is anchored to the respective front edges of the inner and outer power-net (elastic) fabric panels in-combination with an underlying, inelastic hook-and-eye cotton guard-tape system comprising a wide soft cotton guard tape secured by an inelastic seam to the front edges of the inner and outer power-net fabric panels on one side of the opening torso sleeve, that underlies the zipper opening, and an inelastic bias tape securely sewn along and joining the front edges of the fabric panels on the other (opposite) side of the opening torso sleeve spaced back from the zipper. The guard tape presents hooks longitudinally spaced along one side of the opening torso sleeve adjacent the zipper. The bias tape has corresponding eyes spaced back from the zipper. The hook-and-eye cotton guard-tape system eases closing and opening torso sleeve by sequentially engaging the hooks and eyes then advancing the zipper when closing the sleeve and visa versa when opening the torso sleeve.

The non-zippered embodiment of the high-back gluteal shaping compression garment (See FIGS. 7a, 7b 7c & FIG. 10b) has a central front, elastic and faggot stitch seam (FIG. 7a) that joins folded-back edges of the left and right front torso sections of the inner and outer elastic power-net fabric panels together forming a torso sleeve with an open top. A shaped, abdominal, power-net fabric, tummy panel with symmetrical left and right side edges is secured by elastic seams within the compression garment centrally underlying the front, elastic and faggot stitch seam (FIG. 7b) between the open crotch and the front inframammary top of the formed torso sleeve. Those artisan skilled in art of compression garment design, should appreciate that the symmetrical configurations of tummy panels can be varied for increasing areas of tension across the abdomen of a patient post surgery, thus creating pressure gradients in the underlying abdominal tissues for moving seeping body fluids following liposuction procedures to drain locations for mitigating formation of seromas in the abdominal regions.

I claim:

1. A post surgery medical compression garment for applying compressive forces around a torso, buttocks and thighs of a human being comprising, in combination:
   a) symmetrical (left and right) outer elastic power-net fabric panels each having a top, a torso section, a thigh section, a bottom, a front and a back with:
      (i) a top underarm cutout between a front and a back shoulder-strap anchor tab;
      (ii) a back scalloped collar cutout,
      (iii) a front inframammary cutout for establishing a front inframammary top of the garment;
      (iv) a front crotch opening cutout;
      (v) a front torso section edge extending between the front inframammary cutout and the front crotch opening cutout;
      (vi) a back gluteal cutout;
      (vii) a back torso section edge extending between the back scalloped collar cutout and the back gluteal cutout;
      (viii) a front thigh section edge extending from the front crotch opening cutout to the bottom of each power-net fabric panel, and a back thigh section edge extending from the back gluteal cutout to the bottom of each power-net fabric panel;
   b) symmetrical (left and right) molded, gluteal-shaping, elastic power-net fabric domes each having a bottom cutout for a crotch opening;
   c) elastic seams respectively joining the symmetrical (left and right) molded, gluteal-shaping, elastic power-net fabric domes to corresponding left and right back gluteal cutouts of the symmetrical (left and right) outer elastic power-net fabric panels;

d) a central back elastic seam joining:
  (i) the back torso section edges of the left and right torso sections of the outer elastic power-net fabric panels together and;
  (ii) adjacent edges of the left and right molded, gluteal-shaping, elastic power-net fabric domes below the left and right torso sections together extending to the bottom cutouts of the respective domes for the crotch opening;
e) elastic thigh seams respectively joining the front and back thigh section edges of the left and of the right thigh sections forming left and right thigh compression sleeves, and an elliptically shaped crotch opening in cooperation with the bottom crotch cutouts of the left and right molded, gluteal-shaping, elastic power-net fabric domes;
f) reinforced elastic edge seams secured around bottom end edges of the formed left and right thigh compression sleeves;
g) a reinforcing, folded elastic fabric strip secured by a zigzag stitch seam around the elliptically shaped crotch opening;
h) a central front, elastic faggot stitch seam joining the front torso section edges of the left and right torso sections together forming a torso sleeve having an open top with left and right underarm reliefs between front and back shoulder-strap anchor tabs, an scalloped back collar and a front elastic inframammary top for compressing the torso, tummy and thighs of a human being, in combination with joined symmetrical, left and right molded, gluteal-shaping, elastic power-net fabric domes; and
i) a reinforced elastic edge seam around the open top of the formed torso sleeve.

2. The post surgery medical compression garment of claim 1 for applying compressive forces around a torso, buttocks and thighs of a human being further including symmetrical (left and right) reinforcing elastic power-net fabric torso panels each having:
  (i) a top edge conforming to, and secured by the reinforced elastic edge seam around the top of the torso sleeve;
  (ii) a front torso section edge respectively conforming to the front torso section edge of the corresponding outer elastic power-net fabric panel secured by the central front, elastic faggot stitch seam joining the front torso section edges of the of the outer elastic power-net fabric panels together;
  (iii) an open bottom edge secured by elastic seams to the torso sleeve extending up from the front of the crotch opening along a corresponding left or right, human inguinal—iliac line up and around the torso sleeve to at the elastic seam respectively securing the corresponding back left or right molded, gluteal-shaping, elastic power-net fabric dome;
  (iv) a gluteal relief conforming to a section of the corresponding gluteal cutout of the torso sleeve, secured by the elastic seam securing the corresponding molded, gluteal-shaping, elastic power-net fabric dome to the torso sleeve; and
  (v) a back torso section secured by elastic seams to the elastic power-net fabric of the primary torso sleeve, tapering downward from a back section of the corresponding under-arm cutouts of the torso sleeve terminating at the central back elastic seam of the torso sleeve in a lower back region above elastic power-net fabric domes, and
  (vi) a central lower back edge extending up from the gluteal relief conforming with and secured together by the central back elastic seam of the torso sleeve between, gluteal-shaping, elastic power-net fabric domes.

3. The post surgery medical compression garment of claim 2 further including in combination therewith:
j) a shaped, abdominal, power-net fabric, tummy panel with symmetrical left and right side edges vertically extending up from the crotch opening, to the open top of the torso sleeve centered over the central front elastic faggot stitch seam and secured along its left and right side edges to the torso sleeve by flat elastic seams to the corresponding left and right elastic torso sections of the respective power-net fabric panels.

4. The post surgery medical compression garment of claim 3 further including in combination therewith:
k) adjustable shoulder straps connecting between the left, front and the back shoulder-strap anchor tabs, and the right, front and the back shoulder-strap anchor tabs.

5. A post surgery medical compression garment for applying compressive forces around a torso, buttocks and thighs of a human being comprising, in combination:
a) symmetrical (left and right) outer elastic power-net fabric panels each having a top, a torso section, a thigh section, a bottom, a front and a back with:
  (i) a top underarm cutout between a front and a back shoulder-strap anchor tab;
  (ii) a back scalloped collar cutout,
  (iii) a front inframammary cutout for establishing a front inframammary top of the garment;
  (iv) a front crotch opening cutout;
  (v) a front torso section edge extending between the front inframammary cutout and the front crotch opening cutout;
  (vi) a back gluteal cutout;
  (vii) a back torso section edge extending between the back scalloped collar cutout and the back gluteal cutout;
  (viii) a front thigh section edge extending from the front crotch opening cutout to the bottom of each power-net fabric panel, and a back thigh section edge extending from the back gluteal cutout to the bottom of each power-net fabric panel;
b) symmetrical (left and right) molded, gluteal-shaping, elastic power-net fabric domes each having a bottom cut-out for a crotch opening;
c) elastic seams respectively joining edges of the symmetrical (left and right) molded, gluteal-shaping, elastic power-net fabric domes to corresponding edges of left and right back gluteal cutouts of the symmetrical (left and right) outer elastic power-net fabric panels;
d) a central back elastic seam joining:
  (i) the back torso section edges of the left and right torso sections of the outer elastic power-net fabric panels together and;
  (ii) adjacent edges of the left and right molded, gluteal-shaping, elastic power-net fabric domes together below the left and right torso gluteal cutout locations extending to the bottom cutouts of the domes for the open crotch;
e) elastic thigh seams respectively joining the front and back thigh section edges of the left thigh section and of the right thigh section forming left and right thigh compression sleeves, and an elliptically shaped crotch opening in cooperation with the bottom cutouts of the left and right molded, gluteal-shaping, elastic power-net fabric domes;

f) reinforced elastic edge seams around bottom edges of the formed left and right thigh compression sleeves;

g) a folded reinforcing, elastic fabric strip lining secured by a zigzag stitch seam around the elliptically shaped crotch opening h) means for releasable fastening the front torso section edges of the left and right torso sections of the outer elastic power-net fabric panels together to form an opening torso sleeve with open top with torso left and right torso sections that can be opened and closed between an established front inframammary top to a fastener base above the crotch opening of the garment;

i) a central front elastic seam joining the front torso section edges of the left and right torso sections together between the fastener base and the crotch opening; and j) a reinforced elastic edge seam secured along the open top of the opening torso sleeve, for providing left and right underarm, elastic seamed reliefs between front and back shoulder-strap anchor tabs, an elastic seamed, scalloped back collar and a front elastic inframammary chest seam for compressing the torso, tummy and thighs of a human being, in combination with the joined symmetrical, left and right molded, gluteal-shaping, elastic power-net fabric domes.

6. The post surgery medical compression garment of claim 5 further including symmetrical (left and right) reinforcing elastic power-net fabric torso panels each having:

(i) a top edge conforming to, and secured by the reinforced elastic edge seam around the top of the torso sleeve;

(ii) a front torso section edge respectively conforming to and secured with the front torso section edge of the corresponding outer elastic power-net fabric panel by the central front elastic seam joining the front torso section edges of the left and right torso sections together between the fastener base and the open crotch, and by the means for releasable fastening the front torso section edges of the left and right torso sections of the outer elastic power-net fabric panels together above the fastener base above the front crotch opening cutouts;

(iii) an open bottom edge secured by elastic seams to the torso sleeve extending up from the front of the crotch opening along a corresponding left or right human inguinal—iliac line up and around the torso sleeve to at the elastic seam respectively securing the corresponding left or right molded, back gluteal-shaping, elastic power-net fabric dome;

(iv) a gluteal relief conforming to a section of the corresponding back gluteal cutout of the torso sleeve, secured by the elastic seam securing the corresponding molded, gluteal-shaping, elastic power-net fabric dome to the torso sleeve; and (v) a back torso section secured by elastic seams to the elastic power-net fabric of the primary torso sleeve, tapering downward from a back section of the corresponding under-arm cutouts of the torso sleeve terminating at the central back elastic seam of the torso sleeve in a lower back region above elastic power-net fabric domes, and (vi) a central lower back edge extending up from the gluteal relief conforming with and secured together by the central back elastic seam of the torso sleeve between, gluteal-shaping, elastic power-net fabric domes.

7. The post surgery medical compression garment of claim 6 for applying compressive forces around a torso, buttocks and thighs of a human being wherein the means for releasable fastening the front edges of the left and right torso sections of the outer elastic power-net fabric panels together to form an opening torso sleeve further including, in combination therewith, (i) a wide soft cotton guard tape secured by an inelastic seam to the front edges of the inner and outer power-net fabric panels on one side of the opening torso sleeve, that underlies the zipper opening presenting hooks longitudinally spaced along one side of the opening torso sleeve within the opening of the torso sleeve adjacent the zipper, and (ii) an inelastic bias tape seam joining the front edges of the inner and outer power-net fabric panels on the opposite side of the opening torso sleeve presenting corresponding eyes on the secured to opposite side of the torso sleeve opening behind the opening of the torso sleeve, whereby the torso sleeve can be sequential closed and opened by sequentially engaging the hooks and eyes then advancing the zipper when closing the torso sleeve and visa versa when opening the torso sleeve.

8. The post surgery medical compression garment of claim 7 further including in combination therewith:

k) adjustable shoulder straps connecting between the left, front and the back shoulder-strap anchor tabs, and the right, front and the back shoulder-strap anchor tabs.

9. In a post surgery medical compression garment designed for applying compressive forces around a torso, buttocks, and thighs of a human being including a constructed, elastic, open top, power-net fabric torso sleeve encircling the human torso below an inframammary top with upper and lower back power-net compression sections, front abdominal and pubic power-net compression sections, left and right flank power-net compression sections and having bottom elastic, power-net, fabric thigh sleeves encircling the thighs below a front section of a crotch opening at the base of the torso sleeve, an improved buttocks contouring section comprising, in combination therewith:

a) symmetrical (left and right) molded power-net elastic fabric domes each with a bottom crotch opening cut-out, and having permanent, heat set, power-net, elastic cells that uniformly expand in circumferences toward the top of the dome for establishing a pressure gradient in underlying gluteal tissues that decreases toward the top of the dome;

b) elastic seams securing the respective left and right molded, elastic power-net fabric domes in the buttocks contouring section of the garment, below the low back power-net compression sections, down the respective left and right flank power-net compression sections, and above tops of the respective left and right thigh sleeves to the front section of the crotch opening at the base of the torso sleeve;

c) a central elastic seam securing adjacent edges of the symmetrical (left and right) molded, gluteal-shaping, elastic power-net fabric domes together between the lower back power-net compression sections of the torso sleeve and the respective crotch opening cutouts of the molded, gluteal-shaping, elastic power-net fabric domes; and d) a folded reinforcing, elastic fabric strip lining secured by an elastic seam around an elliptically shaped crotch opening formed by the front section of a crotch opening at the base of the torso sleeve and the respective left and right bottom crotch opening cutouts of the molded elastic power-net fabric domes.

* * * * *